United States Patent
Wade et al.

(10) Patent No.: US 8,926,324 B2
(45) Date of Patent: *Jan. 6, 2015

(54) SYSTEMS AND METHODS FOR RECONDITIONING IMPLANTS IN SITU

(71) Applicants: Curtis K. Wade, Bellingham, WA (US); Charles A. McCoy, II, Bellingham, WA (US)

(72) Inventors: Curtis K. Wade, Bellingham, WA (US); Charles A. McCoy, II, Bellingham, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/023,284

(22) Filed: Sep. 10, 2013

(65) Prior Publication Data

US 2014/0106295 A1 Apr. 17, 2014

Related U.S. Application Data

(63) Continuation of application No. 13/194,590, filed on Jul. 29, 2011, now Pat. No. 8,529,259.

(60) Provisional application No. 61/368,784, filed on Jul. 29, 2010.

(51) Int. Cl.
| | |
|---|---|
| *A61C 3/06* | (2006.01) |
| *A61C 8/00* | (2006.01) |
| *A61C 19/06* | (2006.01) |
| *A61C 1/02* | (2006.01) |
| *A61C 1/08* | (2006.01) |
| *A61C 1/10* | (2006.01) |
| *A61C 17/02* | (2006.01) |

(52) U.S. Cl.
CPC ............... *A61C 8/0089* (2013.01); *A61C 19/06* (2013.01); *A61C 1/02* (2013.01); *A61C 1/084* (2013.01); *A61C 1/10* (2013.01); *A61C 3/06* (2013.01); *A61C 17/0202* (2013.01)
USPC ............................ 433/166; 433/142; 433/173

(58) Field of Classification Search
CPC .............. A61C 3/00; A61C 3/06; A61C 1/00; A61C 1/0084; A61C 8/0089; A61C 19/002; A61C 17/036
USPC ............................ 433/75, 141–143, 166, 173
See application file for complete search history.

(56) References Cited

U.S. PATENT DOCUMENTS

| | | |
|---|---|---|
| 4,547,156 A | 10/1985 | Hader |
| 4,793,808 A | 12/1988 | Kirsch |
| 5,071,350 A | 12/1991 | Niznick |
| 5,071,351 A | 12/1991 | Green, Jr. et al. |
| 5,201,656 A | 4/1993 | Sicurelli |

(Continued)

FOREIGN PATENT DOCUMENTS

SE 533335 C2 * 7/2009 ............. A61B 17/16

*Primary Examiner* — Heidi M Eide
(74) *Attorney, Agent, or Firm* — Michael R. Schacht; Schacht Law Office, Inc.

(57) ABSTRACT

A system for reconditioning a dental implant in situ comprising a buffer member, a drive member, abrasive material, and a sleeve member. The sleeve member moves between first and second positions relative to the buffer member. The buffer member is in an open configuration when the sleeve member is in the first position. The sleeve member holds the buffer member in a closed configuration when the sleeve member is in the second position. The buffer member is rotated such that the plurality of fingers of the buffer member cause the abrasive material to remove at least a portion of the texture layer on the textured portion of implant outer surface of the second implant portion.

17 Claims, 14 Drawing Sheets

(56) References Cited

U.S. PATENT DOCUMENTS

| | | |
|---|---|---|
| 5,667,513 A | 9/1997 | Torrie et al. |
| 5,782,635 A | 7/1998 | Altvater |
| 5,868,572 A | 2/1999 | Lazzara et al. |
| 5,904,483 A | 5/1999 | Wade |
| 7,179,084 B1 | 2/2007 | Kometas |
| RE43,470 E | 6/2012 | Wade |
| 8,529,259 B2 | 9/2013 | Wade et al. |
| 2006/0269901 A1 | 11/2006 | Rosenblood et al. |
| 2009/0246733 A1 | 10/2009 | Auderset et al. |
| 2010/0105006 A1 | 4/2010 | Leike et al. |
| 2010/0291506 A1* | 11/2010 | Olsson et al. ............ 433/143 |

* cited by examiner

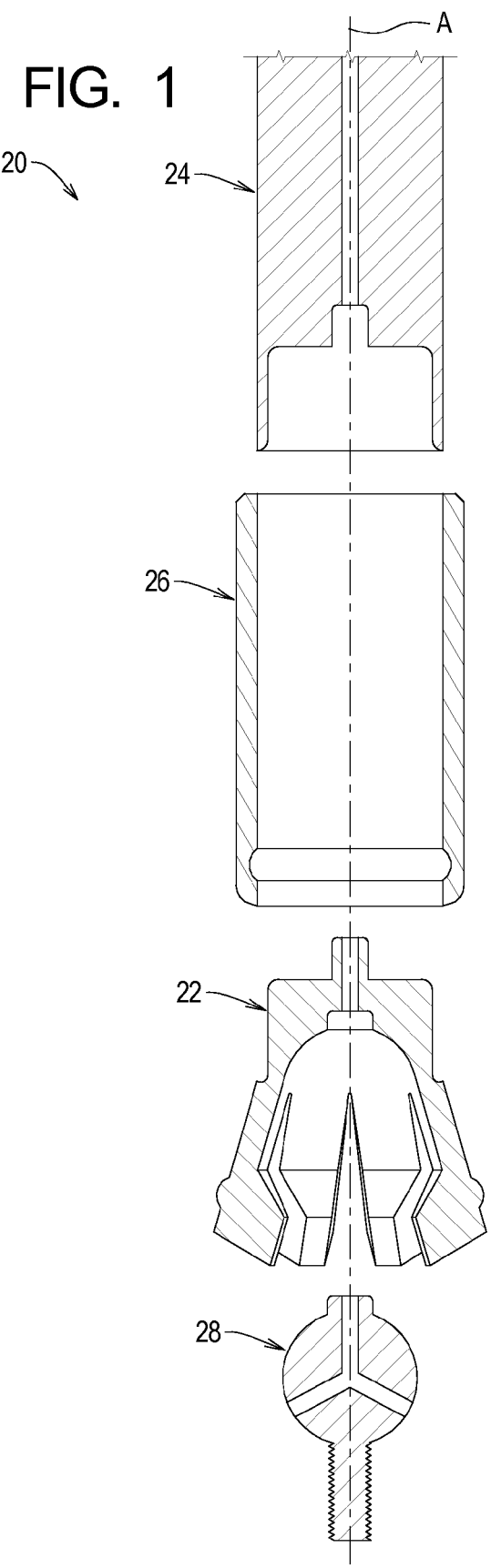

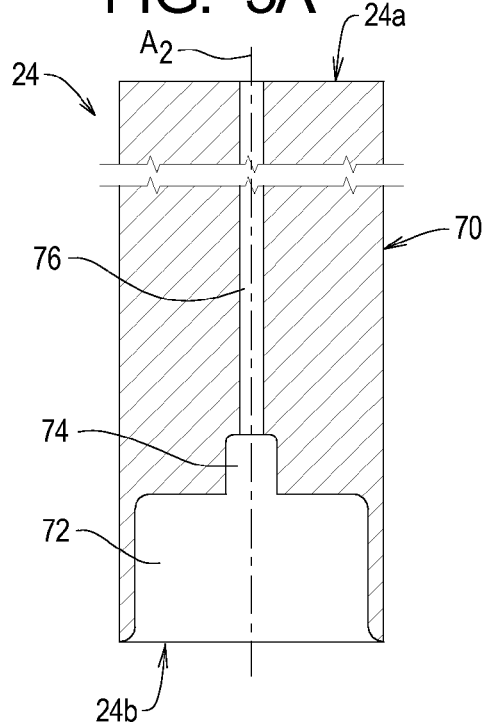
FIG. 3A
FIG. 3B
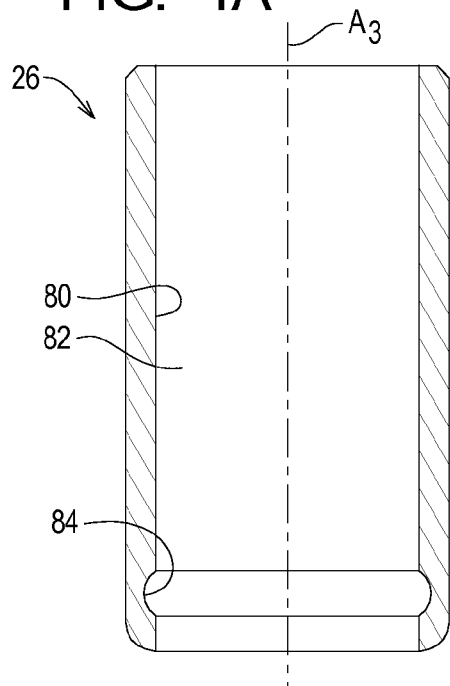
FIG. 4A
FIG. 4B
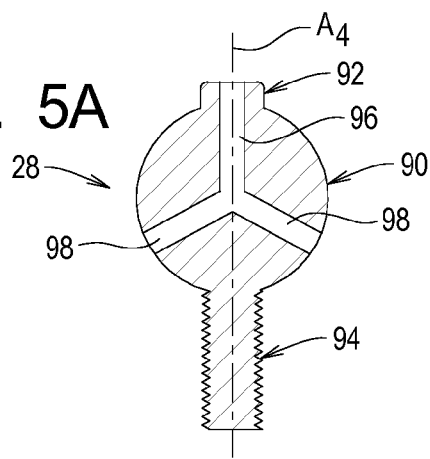
FIG. 5A
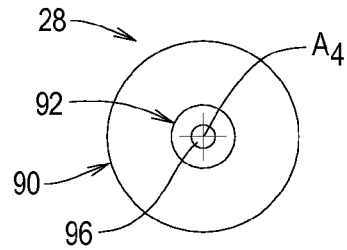
FIG. 5B

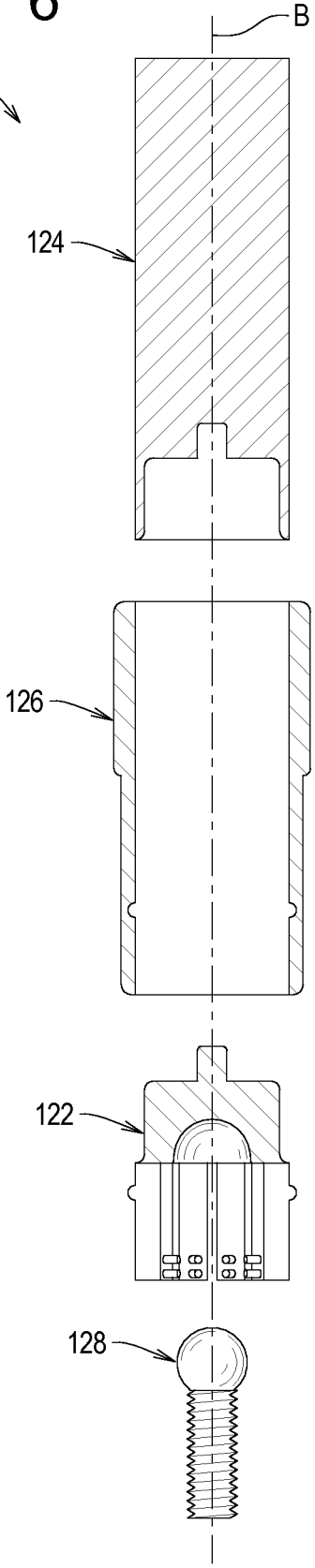

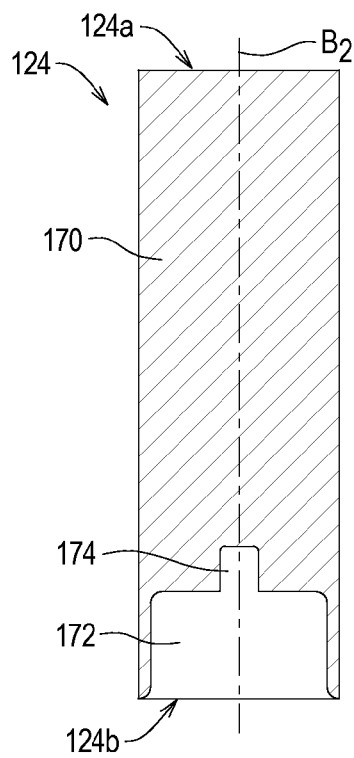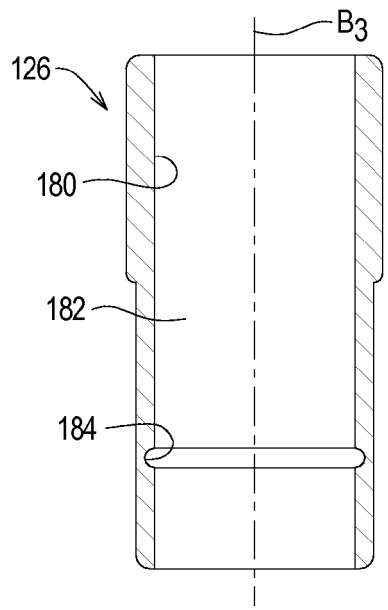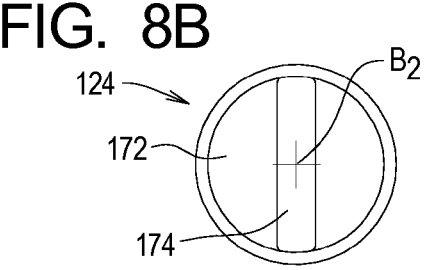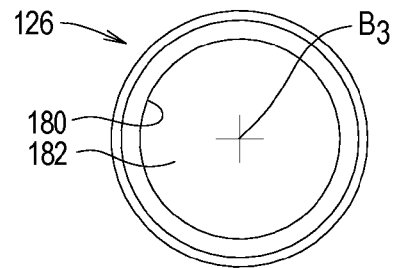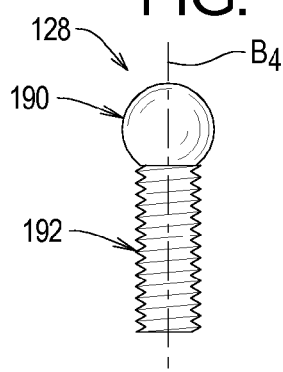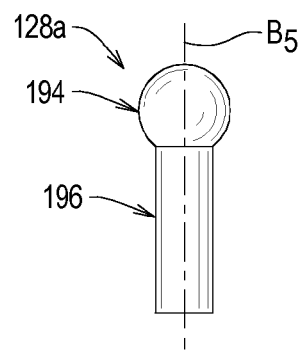

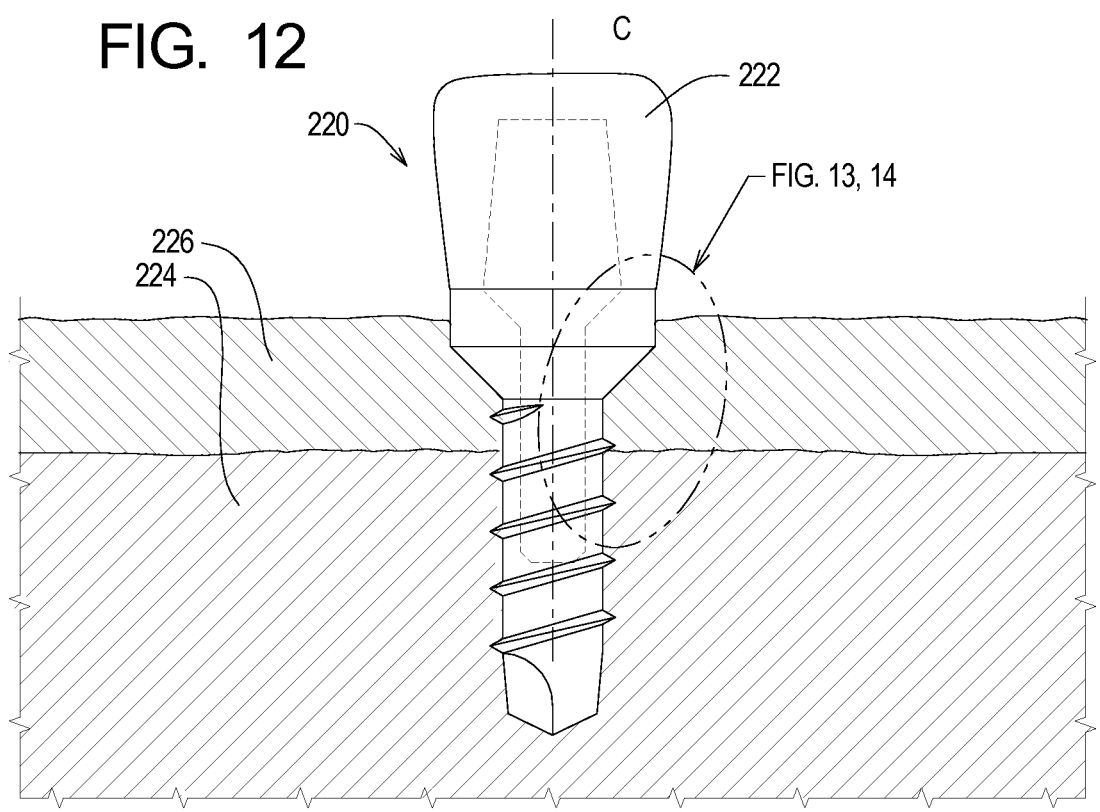

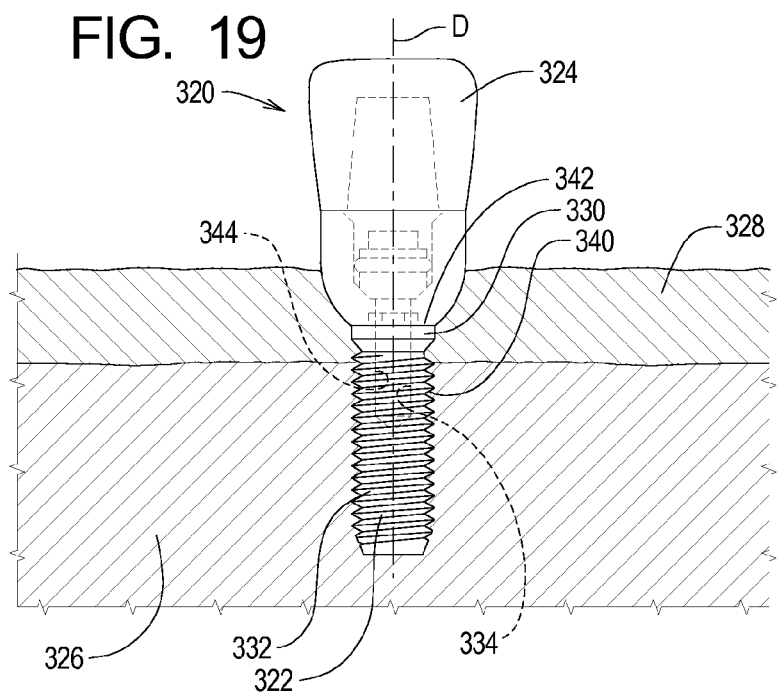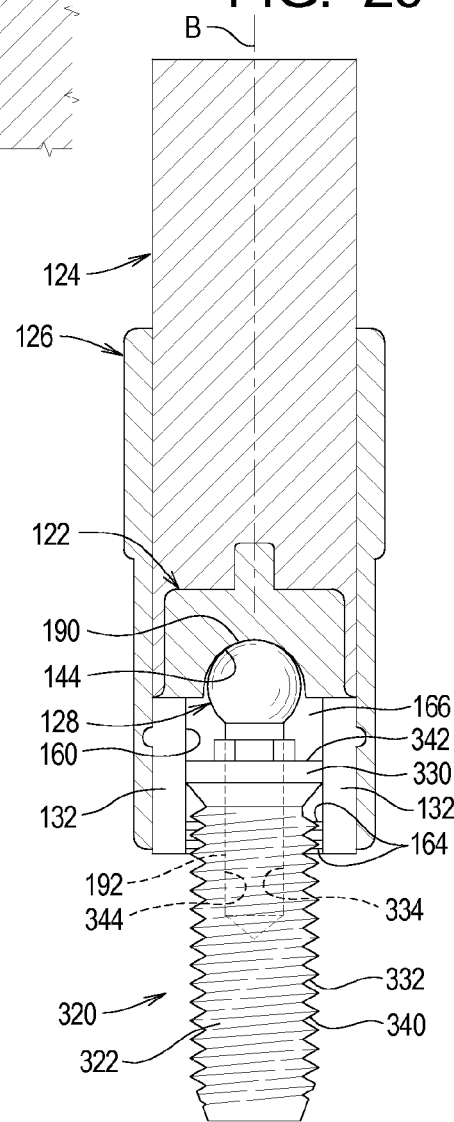

SYSTEMS AND METHODS FOR RECONDITIONING IMPLANTS IN SITU

RELATED APPLICATIONS

This application, U.S. patent application Ser. No. 14/023,284 filed Sep. 10, 2013 is a continuation of U.S. patent application Ser. No. 13/194,590 filed Jul. 29, 2011, now U.S. Pat. No. 8,529,259 which issued Sep. 10, 2013.

U.S. patent application Ser. No. 13/194,590 claims priority benefit of U.S. Provisional Patent Application Ser. No. 61/368,784 filed Jul. 29, 2010.

The contents of all related applications listed above are incorporated herein by reference.

TECHNICAL FIELD

The present invention relates to prosthodontic methods and apparatus and, more specifically, to such methods and apparatus that simplify the making of dental impressions employed to fabricate a restorative tooth prosthesis.

BACKGROUND

Many systems and methods are currently available for replacing lost, removed, or diseased teeth. These systems and methods comprise the following basic steps. First, an implant is threaded into a cavity formed in the patient's jaw at the location of a lost tooth. The implant is then allowed to osseointegrate with the jaw bone. A technician will then fabricate a prosthetic tooth on an abutment member. The abutment member is then attached to the implant to mount the prosthetic tooth at its appropriate location. In this context, the abutment member forms the structural attachment between the prosthetic tooth and the implant, and the prosthetic tooth functionally and aesthetically replaces the exposed portion of the lost tooth.

It should be clear that this basic process can be employed when replacing a plurality of teeth as well as when replacing a single tooth. In the following discussion, the present invention is described in the context of a single tooth, but the principles of the present invention are equally applicable to the situations in which more than one tooth has been replaced.

In certain situations, conditions within the mouth result in an adverse change in the condition of the implant, the abutment member, and/or mouth around the implant and abutment member. When such conditions might be present, the need exists for systems and methods of reconditioning the implant and/or abutment member in situ to avoid or reverse such adverse changes.

SUMMARY

The present invention may be embodied as a system for reconditioning, in situ, a dental implant defining an implant axis and comprising a first implant portion, a second implant portion, and an implant outer surface. The first implant portion is located farther from the implant axis than the second implant portion. A texture layer is formed on at least a textured portion of the implant outer surface. The reconditioning system of the present invention comprises a buffer member, a drive member, abrasive material, and a sleeve member. The buffer member defines a buffer axis and a plurality of fingers and is operable in an open configuration in which the buffer member may be placed over a portion of the implant in a closed configuration in which the buffer member is in contact with the portion of the implant. The drive member is adapted to engage the buffer member such that rotation of the drive member is transferred to the buffer member. The abrasive material is capable of abrading the implant to remove at least a portion of the implant. The sleeve member moves between first and second positions relative to the buffer member. The buffer member is in the open configuration when the sleeve member is in the first position. The sleeve member holds the buffer member in the closed configuration when the sleeve member is in the second position. Rotation of the drive member with the drive member engaged with the buffer member and the buffer member in the closed configuration causes rotation of the buffer member such that the plurality of fingers of the buffer member cause the abrasive material to remove at least a portion of the texture layer on the textured portion of implant outer surface of the second implant portion.

The present invention may also be embodied as a system for reconditioning, in situ, a dental implant defining an implant axis and comprising a first implant portion, a second implant portion, and an implant outer surface. The first implant portion is located farther from the implant axis than the second implant portion. A texture layer is formed on at least a textured portion of the implant outer surface. The reconditioning system of the present invention comprises a buffer member, a drive member, and abrasive material. The buffer member defines a buffer axis and a plurality of fingers. The buffer member is operable in an open configuration in which the buffer member may be placed over a portion of the implant and a closed configuration in which the buffer member is in contact with the portion of the implant. The drive member is adapted to engage the buffer member such that rotation of the drive member is transferred to the buffer member. The abrasive material is capable of abrading the implant to remove at least a portion of the implant. A drive passageway is formed in the drive member. A buffer passageway is formed in the buffer member. The drive passageway and the buffer passageway are aligned to define an irrigation passageway through which material may be introduced between the buffer member and the implant. Rotation of the drive member with the drive member engaged with the buffer member and the buffer member in the closed configuration causes rotation of the buffer member such that the plurality of fingers of the buffer member cause the abrasive material to remove at least a portion of the texture layer on the textured portion of implant outer surface of the second implant portion.

The present invention may also be embodied as a method of reconditioning, in situ within a patient's mouth, a dental implant defining an implant axis and comprising a first implant portion, a second implant portion, and an implant outer surface. The first implant portion is located farther from the implant axis than the second implant portion. A texture layer is formed on at least a textured portion of the implant outer surface. The example method comprises the following steps. At least one of tissue and bone is removed to expose at least a portion of the second implant portion of the dental implant. A buffer member defining a buffer axis and a plurality of fingers is provided. The buffer member is operable in an open configuration in which the buffer member may be placed over a portion of the implant and a closed configuration in which the buffer member is in contact with the portion of the implant. A sleeve member is arranged in a first position relative to the buffer member such that the buffer member may be placed in in the open configuration. The buffer member is arranged in the open configuration. The buffer member is displaced such that the first implant portion passes between the tip portions of the plurality of fingers. The buffer member is arranged in the closed configuration such that tip portions of the plurality of fingers are adjacent to the second implant portion. The sleeve member is arranged in a second position relative to the buffer member to hold the buffer member in the closed configuration. Abrasive material capable of removing at least a portion of the implant is provided. The buffer member is rotated such that the plurality of fingers cause the abrasive material to abrade the second implant portion to remove at least a portion of the texture layer on the textured portion of implant outer surface of the second implant portion.

BRIEF DESCRIPTION OF THE DRAWINGS

FIG. 1 is an exploded view of a first example reconditioning system of the present invention;

FIG. 3A is a section view of a first example drive member of the first example reconditioning system;

FIG. 3B is a bottom plan view of the first example drive member;

FIG. 4A is a section view of a first example sleeve member of the first example reconditioning system;

FIG. 4B is a bottom plan view of the first example sleeve member;

FIG. 5A is a section view of a first example guide member used by the first example reconditioning system;

FIG. 5B is a top plan view of the first example guide member;

FIG. 6 is an exploded view of a second example reconditioning system of the present invention;

FIG. 8A is a section view of a second example drive member of the first example reconditioning system;

FIG. 8B is a bottom plan view of the second example drive member;

FIG. 9A is a section view of a second example sleeve member of the second example reconditioning system;

FIG. 9B is a bottom plan view of the second example sleeve member;

FIG. 10 is a side elevation view of a second example guide member of the second example reconditioning system;

FIG. 11 is a side elevation view of a third example guide member that may be used by the second example reconditioning system in place of the second example guide member;

FIG. 12 is a side elevation, partial section view of a first example type of implant member in situ;

FIG. 19 is a side elevation, partial section view illustrating a second example type of implant member in situ;

FIG. 20 is a side elevation, partial section view of illustrating the use of the second example reconditioning system to recondition the second example implant member of FIG. 19 in situ according to the principles of the present invention.

DETAILED DESCRIPTION

I. Introduction

Figure 2A:
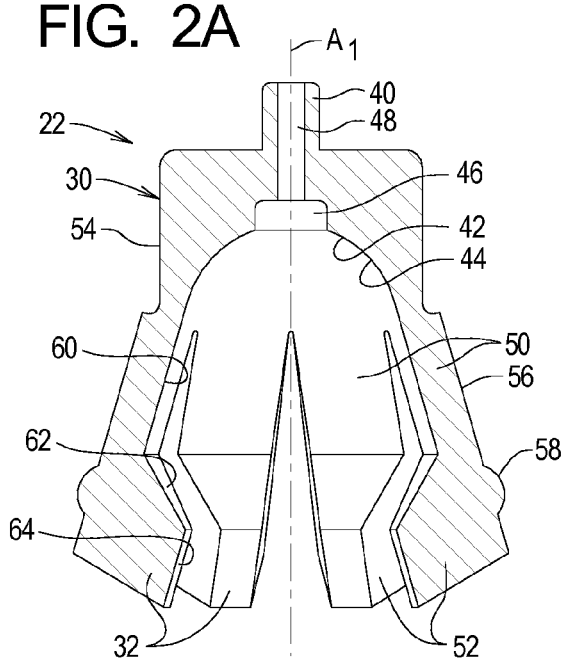
FIG. 2A is a section view of a first example buffer member of the first example reconditioning system in an open configuration.

In the following discussion, first, second, and third example reconditioning systems of the present invention will be described. Example methods of using the first and second example reconditioning systems will then be presented. Finally, certain variations on the systems and methods described herein will be presented.

II. First Example Reconditioning System

Referring initially to FIG. 1 of the drawing, depicted therein is a first example implant reconditioning system 20 constructed in accordance with, and embodying, the principles of the present invention. The first example system 20 comprises a buffer member 22, a drive member 24, a sleeve member 26, and a guide member 28. The first example implant reconditioning system 20 defines a first system axis A.

In use, the guide member 28 supports the buffer member 22 in a desired position relative to an implant to be reconditioned (not shown in FIG. 1). The driver member 24 engages the buffer member 22 and rotates the buffer member 22 relative to the implant. The sleeve member 26 is disengaged to allow the buffer member 22 to be placed in an open configuration in which the buffer member 22 may be arranged in the desired position; the sleeve member 26 is then placed in an engaged position to hold the buffer member 22 is a closed configuration around the implant. As the buffer member 22 is held in the closed configuration around the implant and rotated relative thereto, the buffer member 22 causes the implant member to be reconditioned.

FIGS. 2A-2E illustrate that the first example buffer member 22 comprises a base portion 30 and a plurality (two or more) of fingers 32 and defines a buffer member axis $A_1$. A drive boss 40 extends from the base portion 30 generally along the buffer member axis $A_1$. As perhaps best shown in FIG. 2D, the drive boss 40 is longer in a first lateral direction than in a second lateral dimension; the exact shape of the drive boss 40 is, however, not critical so long as it functions to transfer torque as described below.

An interior surface 42 of the base portion 30 defines a seat surface 44. The seat surface 44 is generally circular and symmetrically arranged about the buffer member axis $A_1$. An alignment cavity 46 extends inwardly from the interior surface 42 generally along the buffer member axis $A_1$. The example base portion 30 depicted in FIGS. 2A-2E further comprises a buffer passageway 48 that also generally extends in the direction of the buffer member axis $A_1$.

The fingers 32 comprise extension portions 50 and tip portions 52. Formed on an outer surface 54 of the buffer member 22 are a step surface 56 (at the base of the fingers 32) and sleeve detent(s) 58 (on the tip portions 52 of the fingers 32).

The extension portions 50 define first inner surface portions 60, while the tip portions 52 define second and third inner surface portions 62 and 64. The second surface portions 62 extend between the first and third inner surface portions 60 and 64 of each of the fingers 32.

Figure 2B:
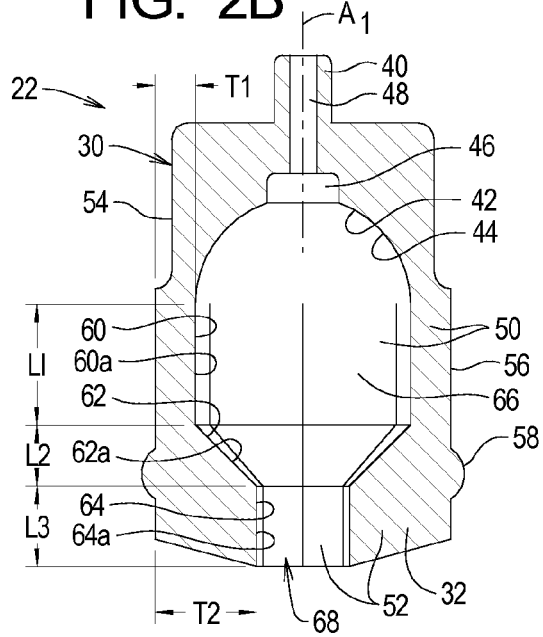
FIG. 2B is a section view of the first example buffer member in a closed configuration.
Figure 2C:
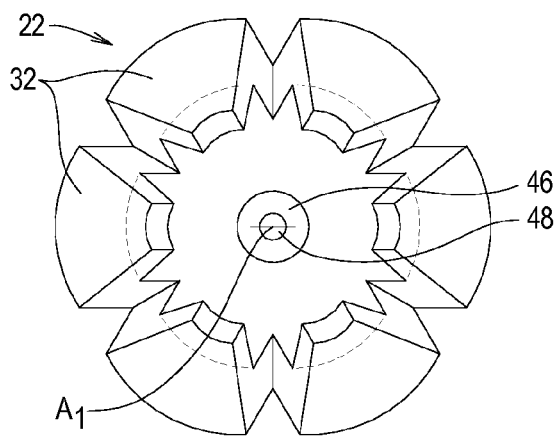
FIG. 2C is a bottom plan view of the first example buffer member in the open configuration.

As perhaps best shown in FIG. 2B, the extension portions 50 have a first thickness dimension t1 and a first length dimension l1 and the tip portions 52 have a second thickness dimension t2 and a second and third length dimensions l2 and l3. For reasons that will become apparent from the following discussion, the relative dimensions of the extension portions 50 and tip portions 52 are typically selected based on the dimensions of the implant to be reconditioned.

Figure 2D:
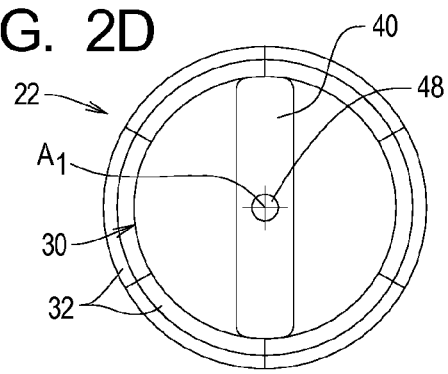
FIG. 2D is a top plan view of the first example buffer member in the closed configuration.
Figure 2E:
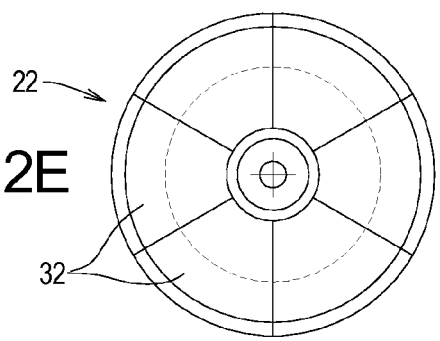
FIG. 2E is a bottom plan view of the first example buffer member in the closed configuration.

The buffer member 22 is configured such that the fingers 32 can be moved relative to the buffer member axis $A_1$ between an open configuration (FIG. 2A, 2C) and a closed configuration (FIGS. 2B, 2D, and 2E). Typically, the entire buffer member 22 is made of a resilient material that can be deformed to move the fingers 32 between the open and closed configurations.

As shown in FIG. 2B, with the example buffer member 22 in the closed configuration, the first, second, and third inner surface portions 60, 62, and 64 are arranged to define substantially contiguous first, second, and third buffer surfaces 60a, 62a, and 64a, and these buffer surfaces 60a, 62a, and 64a define a buffer chamber 66. In addition, the third buffer surface 64a defines a buffer opening 68. FIG. 2B further illustrates that the buffer chamber 66 is in fluid communication with the alignment cavity 46 and that, in turn, the alignment cavity 46 is in fluid communication with the buffer passageway 48.

In this closed configuration, the first inner surface portions 60 of opposing fingers 32 are spaced from each other a distance greater than a distance between the third inner portions 64 of the opposing fingers 32. Also, in this closed configuration the example first and third inner surface portions 60 and 64 are substantially parallel to the buffer system axis $A_1$, while the second inner surface portions 62 are angled with respect to the buffer axis $A_1$.

Turning now to FIGS. 3A and 3B, depicted therein are details of the first example drive member 24 of the first example implant reconditioning system 20. The example drive member 24 comprises an elongate shaft 70 defining a drive axis $A_2$. The drive member 24 further defines a base cavity 72, a boss cavity 74, and a drive passageway 76. The base cavity 72 and drive passageway 76 are substantially symmetrically arranged along the drive axis $A_2$. Like the drive boss 40, the boss cavity 74 is longer in a first lateral direction than in a second lateral dimension. Further like the drive boss 40, the exact shape of the boss cavity 74 is not critical. Although the exact shapes of the drive boss 40 and boss cavity 74 are not important, the boss cavity 74 should receive the drive boss 40 such that axial rotation of the drive member 24 is efficiently transferred to the buffer member 22 as will be described in further detail below.

Turning now to FIGS. 4A and 4B of the drawing, depicted in more detail therein is the first example sleeve member 26 of the first example implant reconditioning system 20. The sleeve member 26 defines a drive axis $A_3$ and an interior wall 80; the interior wall 80 in turn defines a sleeve passageway 82. Formed in the interior wall 80 towards one end of the sleeve passageway 82 is a detent groove 84.

FIGS. 5A and 5B depict the guide member 28 of the first example implant reconditioning system 20. The example guide member 28 defines a guide axis $A_4$ and comprises a seat portion 90, an alignment portion 92, and an anchor portion 94. Extending through the guide member 28 is a first guide passageway 96 and one or more second guide passageways 98. The first guide passageway 96 extends through the alignment portion 92 and is in fluid communication with the second guide passageway(s) 98. The second guide passageway(s) 98 extend through the bottom of the seat portion 90 at an angle with respect to the guide axis $A_4$.

The seat portion 90 is sized and dimensioned to engage the seat surface 44 of the buffer member 22 with the alignment portion 92 received within the alignment cavity 46. The example anchor portion 94 is threaded to engage the implant to be reconditioned as will be described in further detail below.

The first example implant reconditioning system 20 is assembled generally as follows. The anchor portion 94 of the guide member 28 is engaged with the implant (as will be described in further detail below), and the buffer member 22 is attached to the drive member 24 to form a first installation unit. The first installation unit is then attached to the sleeve member 26 to form a second installation unit. The second installation unit is then attached to the guide member 28 supported by the implant.

To attach the buffer member 22 to the drive member 24, the buffer member 22 and drive member 24 are then arranged such that the buffer axis $A_1$ and drive axis $A_2$ are aligned with each other. The buffer member 22 is then displaced relative to the drive member 24 such that the base portion 30 of the buffer member 22 is inserted into the base cavity 72 of the drive member 24. When the base portion 30 is fully received within the base cavity 72, the drive boss 40 is also received within the boss cavity 74. And when the drive boss 40 is received in the boss cavity 74, the drive passageway 76 is substantially aligned with the buffer passageway 48. Fluid flow may thus flow between a distal end 24a of the drive member 24 and the alignment cavity 46. Additionally, a proximal end 24b of the drive member 24 engages the step surface 56 when the base portion 30 is completely received within the base cavity 72. At this point, the first installation unit is formed.

After the buffer member 22 has been attached to the drive member 24, the sleeve member 26 is arranged such that the sleeve axis $A_3$ is aligned with the buffer axis $A_1$ and the drive axis $A_2$. The buffer member 22 and drive member 24 are then displaced such that the distal end 24a of the drive member 24 enters the sleeve passageway 82. The buffer member 22 and the drive member 24 are inserted through the sleeve passageway 82 until the distal end 24a exits the passageway 82 and the detent groove 84 is generally aligned with the base portion 30 of the buffer member 22. At this point, the second installation unit has been formed.

The second installation unit is initially in a pre-installation configuration in which the buffer member 22 is in the open configuration. By displacing the sleeve member 26 relative to the buffer member 22 such that the sleeve detent(s) 58 enter the detent groove 84, the second installation unit may be placed into an installation configuration.

The buffer member 22, drive member 24, and sleeve member 26 forming the second installation unit in the pre-installation configuration are then displaced such that the seat surface 44 of the buffer member 22 engages the seat portion 90 of the guide member 28. Because the second installation unit is in the pre-installation configuration (i.e., the buffer member 22 is in the open configuration), the seat portion 90 may pass between the fingers 32 of the buffer member 22. With the seat portion 90 engaged with the seat surface 44, the alignment portion 92 of the guide member 28 is within the alignment cavity 46. In addition, after the seat portion 90 is engaged with the seat surface 44, the sleeve member 26 is displaced to place the second installation unit in the installation configuration (i.e., the buffer member 22 is in the closed configuration). At this point, the seat portion 90 is arranged within the buffer chamber 66.

With the second installation unit in the installation configuration and the seat portion 90 of the guide member 28 within the buffer chamber 66 of the buffer member 22, the first example reconditioning system 20 is in a use configuration. In the use configuration, axial rotation of the drive member 24 causes axial rotation of the buffer member 22. In general, axial rotation of the buffer member 22 causes the implant being reconditioned to be abraded. For example, the tip portions 52 of the fingers 32 may abrade the implant directly and/or the tip portions 52 may cause an abrasive material to abrade the implant indirectly. Examples of the abrasion process will be described in further detail below.

In addition, when the example system 20 is in the use configuration, the drive passageway 76 is aligned with the buffer passageway 48, and the buffer passageway 48 is in turn aligned with the first guide passageway 96. The first example reconditioning system 20 thus forms an irrigation passageway that extends through the drive passageway 76, the buffer passageway 48, the first guide passageway 96, and second guide passageway(s) 98. Accordingly, irrigation fluid may be forced through the irrigation passageway and into the buffer chamber 66 as the buffer member 22 is rotated. The irrigation fluid may cool the various components of the system 20 and/or the implant being reconditioned; the irrigation fluid may also carry away waste material from the reconditioning process. In particular, fluid through the buffer chamber 66 may flow to the exterior of the buffer member 22 through the buffer opening 68 and, under certain circumstances, between the fingers 32.

III. Second Example Reconditioning System

Referring initially to FIGS. 6-11 of the drawing, depicted therein is a second example implant reconditioning system 120 constructed in accordance with, and embodying, the principles of the present invention. The second example system 120 comprises a buffer member 122, a drive member 124, a sleeve member 126, and a guide member 128. The second example implant reconditioning system 120 defines a second system axis B.

In use, the guide member 128 supports the buffer member 122 in a desired position relative to an implant to be reconditioned (not shown in FIGS. 6-11). The driver member 124 engages the buffer member 122 and rotates the buffer member 122 relative to the implant. The sleeve member 126 is disengaged to allow the buffer member 122 to be placed in an open configuration to facilitate arrangement of the buffer member 122 in the desired position; the sleeve member 126 is then placed in an engaged position to hold the buffer member 122 is a closed configuration around the implant. As the buffer member 122 is held in the closed configuration around the implant and rotated relative thereto, the buffer member 122 causes the implant member to be reconditioned.

FIGS. 7A-7D illustrate that the second example buffer member 122 comprises a base portion 130 and a plurality (two or more) of fingers 132 and defines a buffer member axis $B_1$.

Figure 7A:
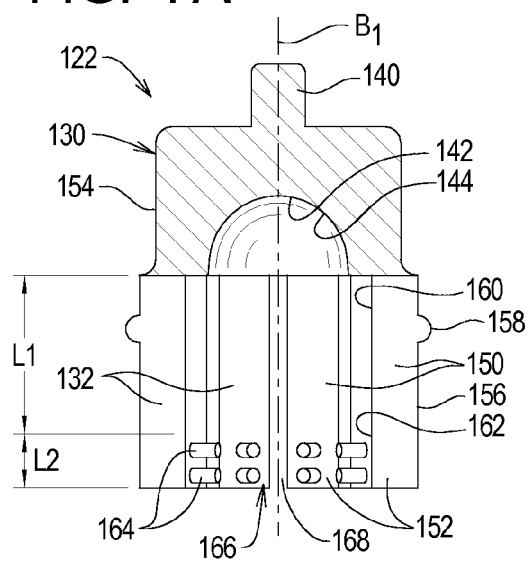
FIG. 7A is a section view of a second example buffer member of the second example reconditioning system in an open configuration.
Figure 7B:
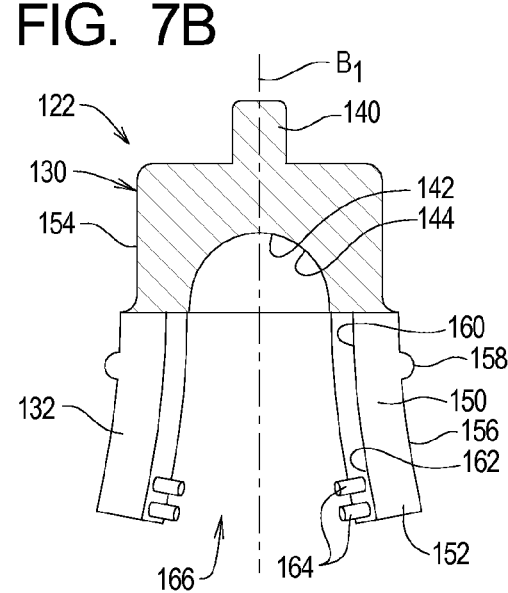
FIG. 7B is a somewhat schematic section view of the second example buffer member in an open configuration.
Figure 7C:
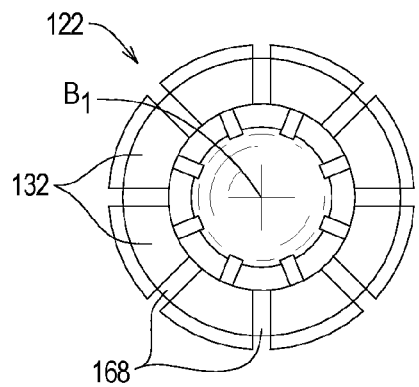
FIG. 7C is a bottom plan view of the second example buffer member in the closed configuration.
Figure 7D:
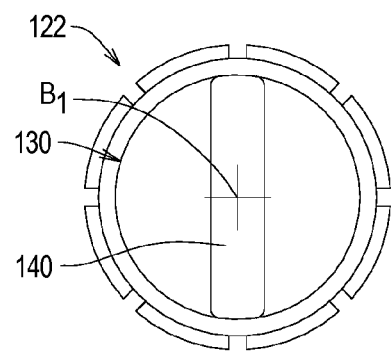
FIG. 7D is a top plan view of the second example buffer member in the closed configuration.

The buffer member 122 is configured such that the fingers 132 can be moved between a closed configuration (FIG. 7A, 7C, 7D) and an open configuration (FIG. 7B). Typically, the entire buffer member 122 is made of a resilient material that can be deformed to move the fingers 132 between the open and closed configurations.

A drive boss 140 extends from the base portion 130 generally along the buffer member axis $B_1$. As perhaps best shown in FIG. 12D, the drive boss 140 is longer in a second lateral direction than in a second lateral dimension; the exact shape of the drive boss 140 is, however, not critical so long as it functions to transfer torque as described below.

An interior surface 142 of the base portion 130 defines a seat surface 144. The seat surface 144 is generally circular and symmetrically arranged about the buffer member axis $B_1$.

The fingers 132 comprise extension portions 150 and tip portions 152. Formed on an outer surface 154 of the buffer member 122 are a step surface 156 (at the base of the fingers 132) and sleeve detent(s) 158 (on the fingers 132 adjacent to the step surface 156).

The extension portions 150 define first inner surface portions 160, while the tip portions 152 each define second inner surface portions 162. Extending from the second inner surface portions 162 are bristles 164. When the buffer member 122 is in its closed configuration as shown in FIG. 7A, the example bristles 164 extend radially inwardly from the fingers 132 towards the buffer member axis $B_1$. The bristles 164 are typically somewhat flexible and are made of or impregnated with abrasive material such as diamond dust capable of abrading the implant as will be described in further detail below.

As perhaps best shown in FIG. 12B, the extension portions 150 have a first length dimension l1 and the tip portions 152 have second length dimensions l2. For reasons that will become apparent from the following discussion, the relative dimensions of the extension portions 150 and tip portions 152 are typically selected based on the dimensions of the implant to be reconditioned.

As shown in FIG. 7B, with the fingers 132 define a buffer chamber 166, and the bristles 164 extend into the buffer chamber 166. In addition, gaps 168 are formed between the fingers 132 with the buffer member 122 in the closed configuration. In this closed configuration, the tips of the bristles 164 of opposing fingers 132 are spaced from each other a distance less than a distance between the first inner surface portions 160 of opposing fingers 132.

Turning now to FIGS. 8A and 8B, depicted therein are details of the second example drive member 124 of the second example implant reconditioning system 120. The example drive member 124 comprises an elongate shaft 170 defining a drive axis $B_2$. The drive member 124 further defines a base cavity 172, and a boss cavity 174. The base cavity 172 is substantially symmetrically arranged along the drive axis $B_2$. Like the drive boss 140, the boss cavity 174 is longer in one lateral direction than in another lateral dimension. Further like the drive boss 140, the exact shape of the boss cavity 174 is not critical. Although the exact shape of the drive boss 140 and boss cavity 174 are not important, the boss cavity 174 should receive the drive boss 140 such that axial rotation of the drive member 124 is efficiently transferred to the buffer member 122 as will be described in further detail below.

Turning now to FIGS. 9A and 9B of the drawing, depicted in more detail therein is the second example sleeve member 126 of the second example implant reconditioning system 120. The sleeve member 126 defines a drive axis $B_3$ and an interior wall 180; the interior wall 180 in turn defines a sleeve passageway 182. Formed in the interior wall 180 towards one end of the sleeve passageway 182 is a detent groove 184.

FIG. 10 depicts the guide member 128 of the second example implant reconditioning system 120. The example guide member 128 defines a guide axis $B_4$ and comprises a seat portion 190 and an anchor portion 192. The seat portion 190 is sized and dimensioned to engage the seat surface 144 of the buffer member 122. The example anchor portion 192 is threaded to engage the implant to be reconditioned as will be described in further detail below.

FIG. 11 depicts an alternative guide member 128a that may be used by the second example implant reconditioning system 120 instead of the guide member 128. The example guide member 128a defines a guide axis $B_5$ and comprises a seat portion 194 and an anchor portion 196. The seat portion 194 is sized and dimensioned to engage the seat surface 144 of the buffer member 122. As will be described in further detail below, the example anchor portion 196 is not threaded, but instead is press fit into the implant to be reconditioned.

The second example implant reconditioning system 120 is assembled generally as follows. The anchor portion 192 of the guide member 128 is engaged with the implant, and the buffer member 122 is attached to the drive member 124 to form a first installation unit. The first installation unit is then attached to the sleeve member 126 to form a second installation unit. The second installation unit is then attached to the guide member 128 supported by the implant.

More specifically, to attach the buffer member 122 to the drive member 124, the buffer member 122 and drive member 124 are arranged such that the buffer axis $B_1$ and drive axis $B_2$ are aligned with each other. The buffer member 122 is then displaced relative to the drive member 124 such that the base portion 130 of the buffer member 122 is inserted into the base cavity 172 of the drive member 124. When the base portion 130 is fully received within the base cavity 172, the drive boss 140 is also received within the boss cavity 174. Additionally, a proximal end 124b of the drive member 124 engages the step surface 156 when the base portion 130 is completely received within the base cavity 172. At this point, the second installation unit is formed.

After the buffer member 122 has been attached to the drive member 124, the sleeve member 126 is arranged such that the sleeve axis $A_3$ is aligned with the buffer axis $B_1$ and the drive axis $B_2$. The buffer member 122 and drive member 124 are then displaced such that the distal end 124a of the drive member 124 enters the sleeve passageway 182. The buffer member 122 and the drive member 124 are inserted through the sleeve passageway 182 until the distal end 124a exits the passageway 182 and the detent groove 184 is generally aligned with the base portion 130 of the buffer member 122. At this point, the second installation unit has been formed.

The second installation unit is initially in a pre-installation configuration in which the buffer member 122 is in the open configuration. By displacing the sleeve member 126 relative to the buffer member 122 such that the sleeve detent(s) 158 enter the detent groove 184, the second installation unit may be placed into an installation configuration.

The buffer member 122, drive member 124, and sleeve member 126 forming the second installation unit in the pre-installation configuration are then displaced such that the seat surface 144 of the buffer member 122 engages the seat portion 190 of the guide member 128. Because the second installation unit is in the pre-installation configuration (i.e., the buffer member 122 is in the open configuration), the seat portion 190 may pass between the fingers 132 of the buffer member 122. In addition, after the seat portion 190 is engaged with the seat surface 144, the sleeve member 126 is displaced to place the second installation unit in the installation configuration (i.e., the buffer member 122 is in the closed configuration). At this point, the seat portion 190 is arranged within the buffer chamber 166.

With the second installation unit in the installation configuration and the seat portion 190 of the guide member 128 within the buffer chamber 166 of the buffer member 122, the second example reconditioning system 120 is in a use configuration. In the use configuration, axial rotation of the drive member 124 causes axial rotation of the buffer member 122. In general, axial rotation of the buffer member 122 causes the implant being reconditioned to be abraded. For example, the bristles 164 extending from the fingers 132 may abrade the implant directly and/or may cause an abrasive material to abrade the implant indirectly. Examples of the abrasion process will be described in further detail below.

Unlike the first example implant reconditioning system 20, the second example implant reconditioning system 120 does not comprise interior passageways that form an irrigation passageway. Accordingly, if used, irrigation fluid is sprayed into the buffer chamber 166 from an external location as the buffer member 122 is rotated. An externally sprayed irrigation fluid may both cool the various components of the system 120 and/or the implant being reconditioned and carry away waste material from the reconditioning process. In particular, externally sprayed fluid will flow into the buffer chamber 166 through the gaps 168 between the fingers 132.

IV. First Example Reconditioning Method

Referring now to FIGS. 12-18 of the drawing, depicted therein is a first example implant member 220 to be reconditioned. The example implant member 220 secures a prosthetic tooth (or teeth) 222 to a jawbone 224 and through soft tissue 226 in a desired orientation within a patient's mouth.

Figure 13:
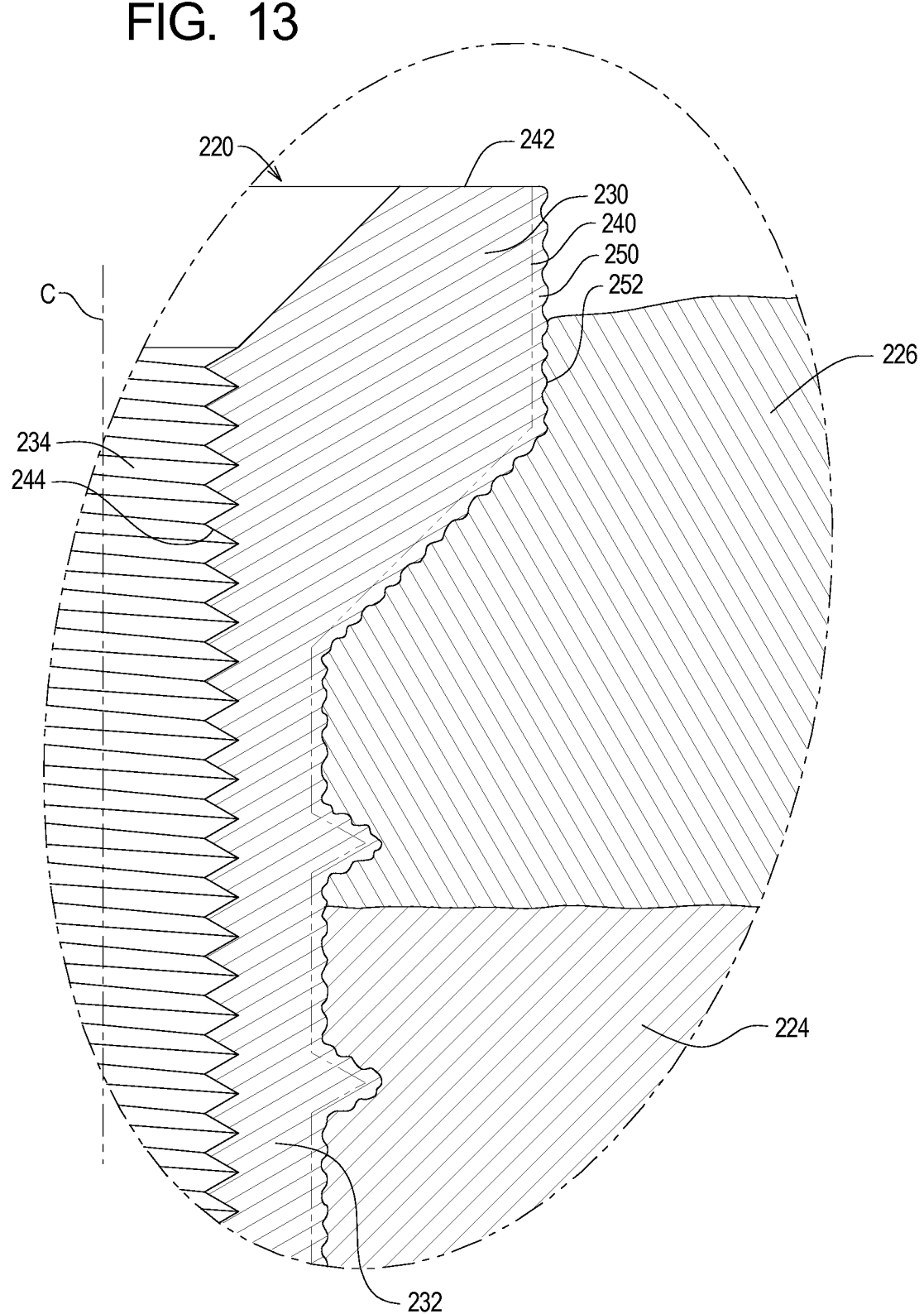
FIG. 13 is an enlarged view of a portion of FIG. 12 illustrating an implant interface between the implant structure and the patient.
Figure 14:
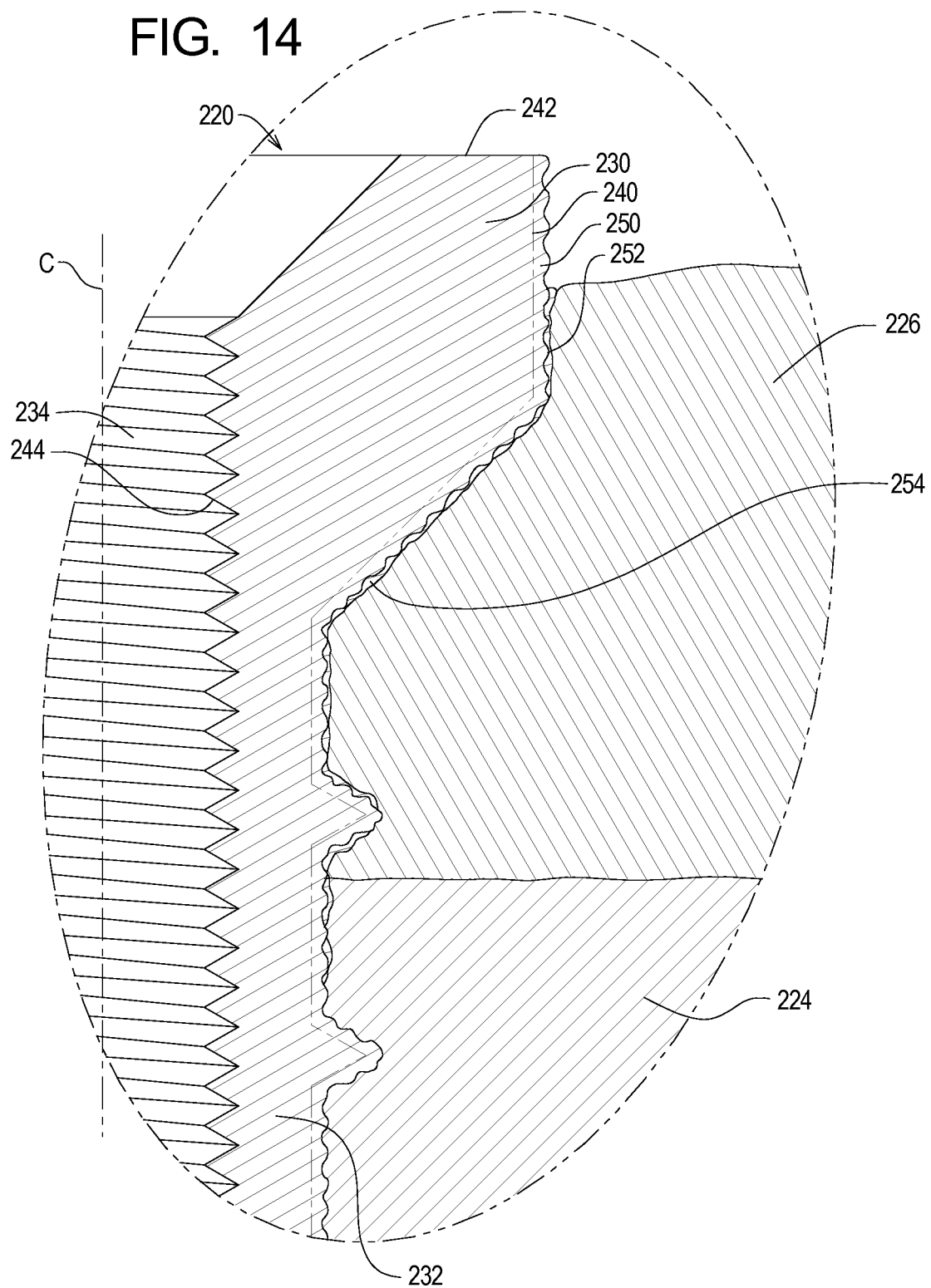
FIG. 14 is an enlarged view similar to that of FIG. 13 illustrating an anomaly at the implant interface.

FIGS. 13 and 14 of the drawing illustrate that the example implant member 220 extends from the jawbone 224 through the soft tissue 226. FIGS. 13 and 14 also show that the implant member 220 defines an implant axis C and comprises a head portion 230, a shaft portion 232, and a bore 234 extending along the implant axis C through the head portion 230 and the shaft portion 232. The implant member 220 further defines an outer surface 240, an upper surface 242, and a bore surface 244. The example bore surface 244 is threaded.

FIGS. 13 and 14 further show that a texture layer 250 is formed on the outer surface 240 of the example implant member 220. FIGS. 13 and 14 further show that an interface region 252 at which the outer surface 240 is adjacent to the jawbone 224 and/or soft tissue 226. Under some conditions, anomalies can develop over time within the interface region 252. In particular, a comparison of FIGS. 13 and 14 illustrate that an anomaly 254 is present within the interface region 252 in FIG. 14 and that no anomaly 254 is presented within the interface region 252 in FIG. 13. Typically, FIG. 13 represents the state of the interface region 252 at an earlier point in time than that depicted in FIG. 14.

Figure 15:
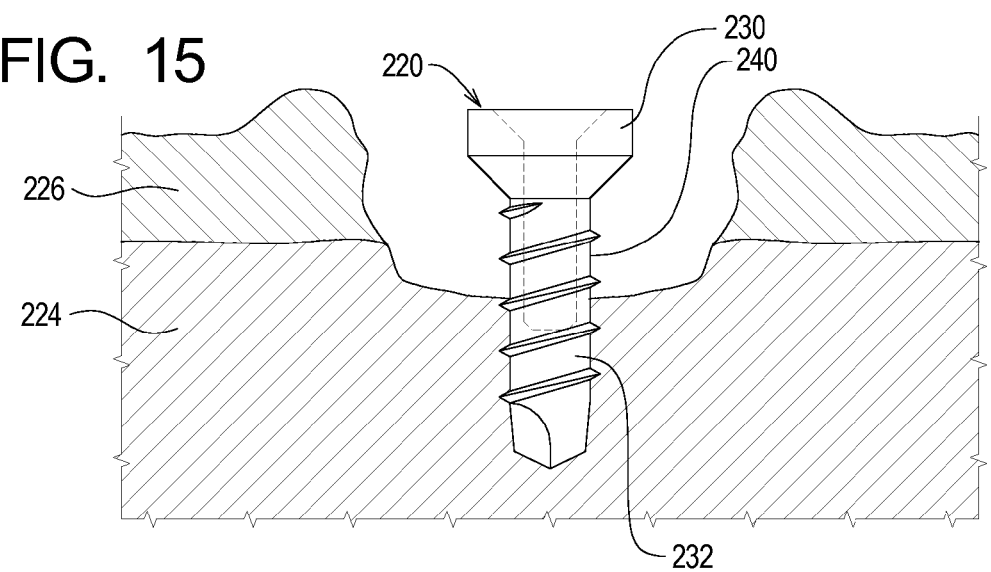
FIG. 15 is a side elevation, partial section view of illustrating the implant structure of FIG. 12 prepared for in situ reconditioning.
Figure 16:
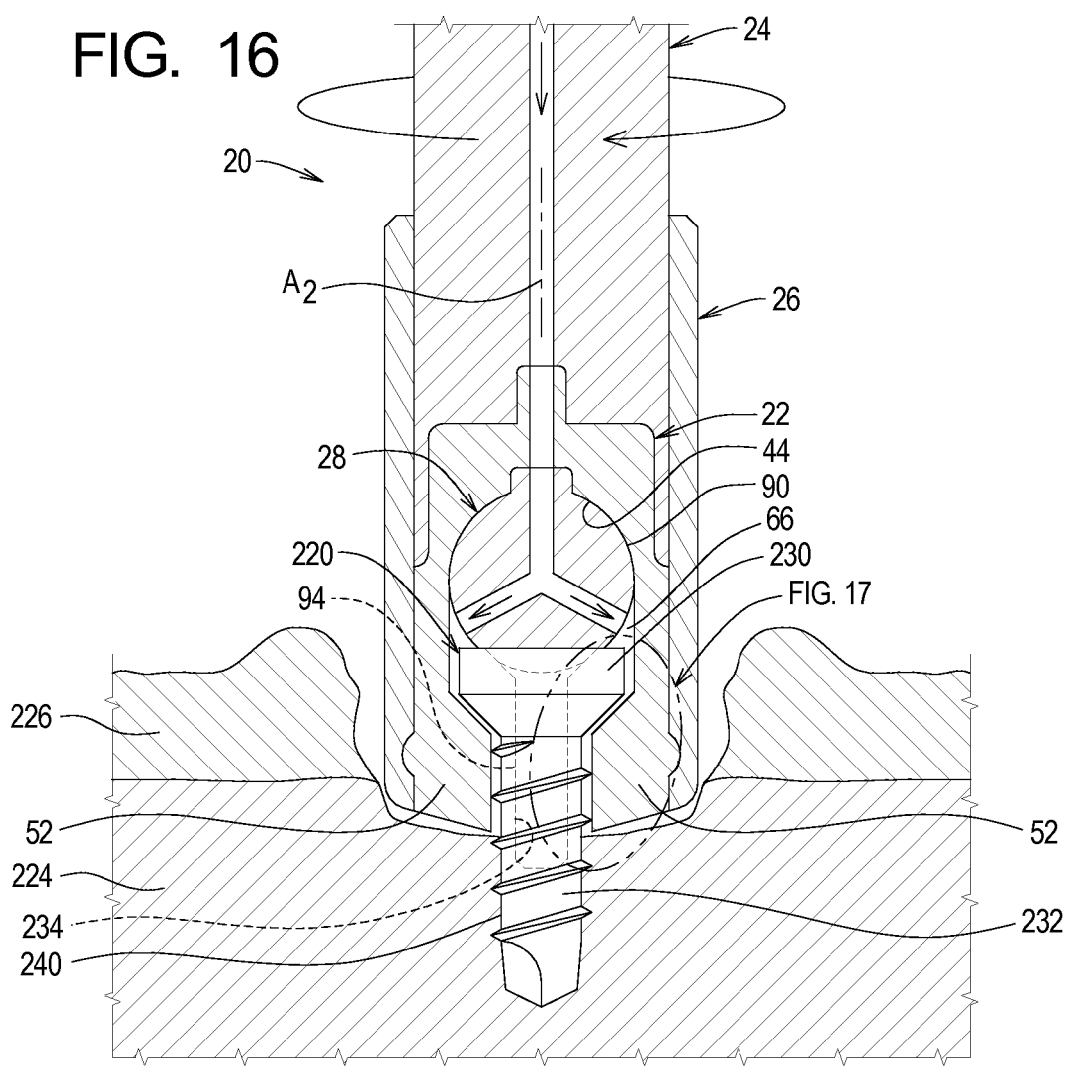
FIG. 16 is a side elevation, partial section view of illustrating the use of the first example reconditioning system to recondition the first example implant member of FIG. 12 in situ according to the principles of the present invention.

Referring now to FIGS. 15 and 16, depicted at 220 therein is an example method of using the first example implant reconditioning system 20 to recondition the implant member 220.

Initially, a portion of the soft tissue 226 is displaced to facilitate access to the head portion 230 and part of the shaft portion 232 of the implant member 220. Then, a trephine or similar tool (not shown) may optionally be used in a generally conventional manner to remove, if necessary, a portion of the jawbone 224 and expose more of the shaft portion 232 and thus the outer surface 240 of the implant member 220.

At this point, the guide member 28 is arranged such that the shaft portion 94 thereof engages the bore 234. In the example method depicted in FIGS. 12-18, both the bore surface 244 and the shaft 94 are provided with matching threads, so the guide member 28 is rotated about its axis $A_1$ to secure the guide member to the implant member 220.

The first example reconditioning system 20 is also provided and arranged as the second installation unit in the pre-installation configuration. In this pre-installation configuration, the buffer member 22 is in the open configuration.

At this point, an abrasive material 260 (FIG. 17) may be applied to the buffer member 22 and, in particular, to the buffer surfaces 60a, 62a, and 64a of the fingers 32. The abrasive material 260 is any material suitable for use in an oral environment that is capable of removing the texture layer 250 when displaced by the buffer member 22 as described herein. Typically, the abrasive material 260 comprises an abrasive agent such as pumice and/or diamond powder. Other materials may be provided to suspend the active abrasive agent in a paste or powder appropriate for use as described herein and to facilitate the function of the abrasive agent.

The reconditioning system 20 is then displaced such that, as shown in FIG. 16, the head portion 230 is within the buffer chamber 66 and the tip portions 52 of the fingers 32 are adjacent to the exposed shaft portion 232. At this point, the seat portion 90 of the guide member 28 engages the seat surface 44 of the buffer member 22 to support the buffer member 28 in a desired relationship with the implant member 220. As described above, with the seat portion 90 in contact with the seat surface 44, the irrigation passageway is formed.

Figure 17:
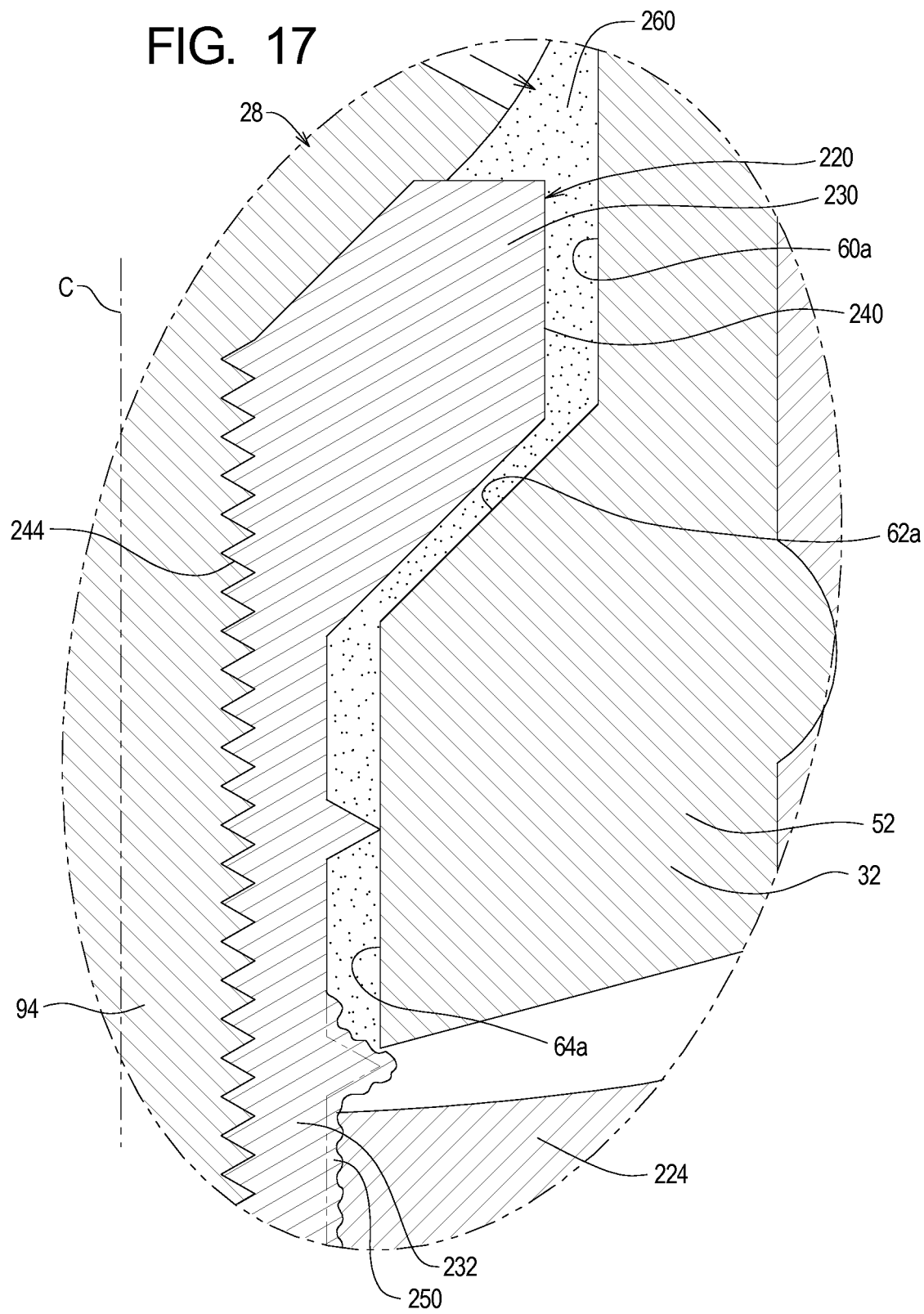
FIG. 17 is an enlarged view of a section of FIG. 16 depicting the flow of abrasive slurry around the implant structure when using the first example reconditioning system.

With the buffer member 28 in this desired relationship, the buffer surfaces 60a, 62a, and 64a defined by the fingers 32 are adjacent to almost the entire portion of the outer surface 240 of the implant member 220 that is not below the surface of the jawbone 224. FIG. 17 illustrates that the abrasive material 260 is arranged between the buffer surfaces 60a, 62a, and 64a and the outer surface 240. The example reconditioning system 20 in the form of the second installation unit is then placed into the installation configuration; at this point, the buffer member 22 is in its closed configuration, and the head portion 230 of the implant member 220 is held within the buffer chamber 66 to inhibit movement of the buffer surfaces 60a, 62a, and 64a away from the outer surface 240 of the implant member 220.

At this point, the drive member 24 is caused to rotate about its axis $A_2$ (which is aligned with the system axis A) as shown in FIG. 16. Axial rotation of the drive member 24 causes the buffer member 22 to rotate about the system axis A relative to the implant member 220. Rotation of the buffer member 22 in turn forces the abrasive material 260 to against the portion of the outer surface 240 not below the surface of the jawbone 224. In this example of the present invention, then, it is not necessary for the buffer surfaces 60a, 62a, and 64a to come into direct contact with the outer surface 240 to abrade this surface 240.

In the example reconditioning system 20, irrigation fluid such as water is forced along the irrigation passageway. This fluid flows through the buffer chamber 66 and around the head portion 230 and shaft portion 232 of the implant member 220. Friction from the abrading process can cause the components of the reconditioning system 20 and the implant member 220 to heat up, and the irrigation fluid can reduce the build-up of such heat. Additionally, the abrading process can create waste material, and the irrigation fluid can remove such waste material.

After a period of time, rotation of the example reconditioning system 20 is ceased, and the system 20 is placed in the pre-installation configuration, thereby placing the buffer member 22 back into its open configuration. The example reconditioning system 20 may then be removed from the implant 220. If the surface 240 has been abraded sufficiently to remove a desired portion of the texture layer 250, the guide member 28 may also be removed from the implant 220. If not, more abrasive material may be applied to the buffer member 22, and at least a portion of the process described above may be repeated.

Figure 18:
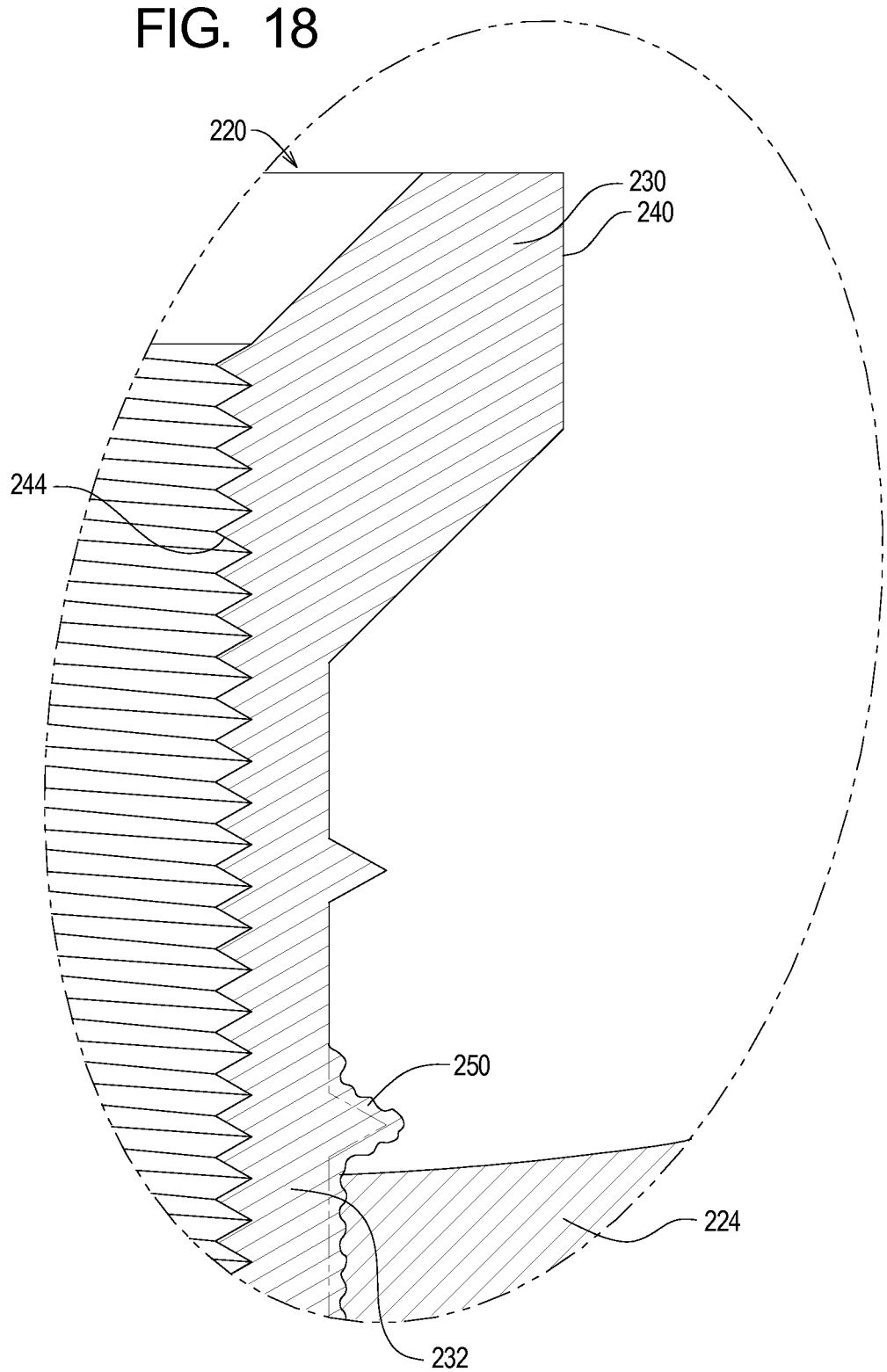
FIG. 18 is an enlarged view similar to that of FIGS. 13 and 14 depicting the first example implant member in a reconditioned state.

After the desired portion of the texture layer 250 is abraded as described above, the implant member 220 will appear as depicted in FIG. 18. In particular, at least a portion of the texture layer 250 has been removed. At this point, the soft tissue 226 can be replaced and the prosthesis 222 may be reattached to the implant member 220.

As described above and depicted in FIGS. 16 and 17, the various abrading surfaces 60a, 62a, and 64a defined by the buffer member 22 define a shape that generally corresponds to the shape and dimensions of the example implant member 220. For an implant member having different shape and dimensions, a different buffer member 22 may be used. Thus buffer members of various dimensions, such as the thickness dimensions t1 and t2 and length dimensions l1, l2, and l3, are provided for use with the typical implant reconditioning system of the present invention.

Accordingly, the first example method described herein will typically comprise the step of selecting a selected buffer member from a plurality of buffer members based on the dimensions of the implant member to be reconditioned and the dimensions of the plurality of buffer members. This step will typically be performed before the step of forming the first installation unit.

V. Second Example Reconditioning Method

Referring now to FIGS. 19 and 20 of the drawing, depicted therein is a second example implant member 320 to be reconditioned. The example implant member 320 secures an abutment member 322 and a prosthetic tooth (or teeth) 324 to a jawbone 326 and through soft tissue 328 in a desired orientation within a patient's mouth.

FIG. 19 of the drawing illustrates that the example implant member 320 extends from the jawbone 326 through the soft tissue 328. FIG. 19 also shows that the implant member 320 defines an implant axis D and comprises a head portion 330, a shaft portion 332, and a bore 334 extending along the implant axis D through the head portion 330 and the shaft portion 332. The implant member 320 further defines an outer surface 340, an upper surface 342, and a bore surface 344. The example bore surface 344 is threaded.

A texture layer (not identified in FIG. 19) is formed on the outer surface 340 of the example implant member 320. As with the implant member 220 described above, under some conditions anomalies can develop over time within an interface region where the texture layer 350 interfaces with the jawbone 326 and the soft tissue 328.

Referring now to FIG. 20, depicted therein is an example method of using the second example implant reconditioning system 120 to recondition the implant member 320.

Initially, a portion of the soft tissue 328 is displaced to facilitate access to the head portion 330 and part of the shaft portion 332 of the implant member 320. Then, a trephine or similar tool (not shown) may optionally be used in a generally conventional manner to remove, if necessary, a portion of the jawbone 326 and expose more of the shaft portion 332 and thus the outer surface 340 of the implant member 320.

At this point, the guide member 128 is arranged such that the shaft portion 192 thereof engages the bore 334. In the example method depicted in FIGS. 19-20, both the bore surface 344 and the shaft 192 are provided with matching threads, so the guide member 128 is rotated about its axis $B_1$ to secure the guide member 128 to the implant member 320. Alternatively, the guide member 128a may be used in place of the guide member 128. In this case, the shaft portion 196 of the guide member 128a is simply pressed into the bore 334 to secure the guide member 128a to the implant member 320.

The second example reconditioning system 120 is also provided and arranged as the second installation unit in the pre-installation configuration. In this pre-installation configuration, the buffer member 122 is in the open configuration. At this point, an abrasive material such as the abrasive material 260 described above may optionally be applied to the buffer member 122 and, in particular, to the inner surface portions 162 and/or bristles 164 of the fingers 132.

The reconditioning system 120 is then displaced such that, as shown in FIG. 20, the head portion 330 is within the buffer chamber 166 and the bristles 164 of the fingers 132 are adjacent to the exposed shaft portion 332. At this point, the seat portion 190 of the guide member 128 engages the seat surface 144 of the buffer member 128 to support the buffer member 128 in a desired relationship with the implant member 320.

With the buffer member 128 in this desired relationship, the inner surfaces 160 defined by the fingers 132 and bristles 164 extending from these fingers 132 are adjacent to almost the entire portion of the outer surface 340 of the implant member 320 that is not below the surface of the jawbone 326. If used, the abrasive material is arranged between the buffer surfaces 160 and the implant outer surface 340.

The example reconditioning system 120 in the form of the second installation unit is then placed into the installation configuration; at this point, the buffer member 122 is in its closed configuration, and the head portion 330 of the implant member 320 is held within the buffer chamber 166 to inhibit movement of the buffer surfaces 160 away from the outer surface 340 of the implant member 320.

At this point, the drive member 124 is caused to rotate about its axis $B_2$ (which is aligned with the system axis B) as shown in FIG. 20. Axial rotation of the drive member 124 causes the buffer member 122 to rotate about the system axis B relative to the implant member 320. Rotation of the buffer member 122 in turn forces the bristles 164 and the abrasive material, if used, against the portion of the outer surface 340 not below the surface of the jawbone 326.

In the example reconditioning system 120, no irrigation passageway is provided, so irrigation fluid such as water is sprayed into the buffer chamber 166 through the gaps 168 formed between the fingers 132. This fluid flows through the buffer chamber 166 and around the head portion 330 and shaft portion 332 of the implant member 320. Friction from the abrading process can cause the components of the reconditioning system 120 and the implant member 320 to heat up, and the irrigation fluid can reduce the build-up of such heat. Additionally, the abrading process can create waste material, and the irrigation fluid can remove such waste material.

After a period of time, rotation of the example reconditioning system 120 is ceased, and the system 120 is placed in the pre-installation configuration, thereby placing the buffer member 122 back into its open configuration. The example reconditioning system 120 may then be removed from the implant 320. If the surface 340 has been abraded sufficiently to remove a desired portion of the texture layer, the guide member 128 may also be removed from the implant 320. If not, more abrasive material may be applied to the buffer member 122, and at least a portion of the process described above may be repeated.

After the desired portion of the texture layer is abraded as described above, the second example implant member 320 will exhibit an appearance similar to that of the first example implant member 220 as depicted in FIG. 18. In particular, at least a portion of the texture layer will have been removed. At this point, the soft tissue 328 can be replaced and the prosthesis 324 may be reattached to the implant member 320.

As described above and depicted in FIG. 20, the abrading surfaces 160 and bristles 164 of the buffer member 122 define a shape that generally corresponds to the shape and dimensions of the example implant member 320. For an implant member having different shape and dimensions, a different buffer member 122 may be used. Thus buffer members of various dimensions are provided for use with the typical implant reconditioning system of the present invention.

Accordingly, the third example method described herein will typically comprise the step of selecting a selected buffer member from a plurality of buffer members based on the dimensions of the implant member to be reconditioned and the dimensions of the plurality of buffer members. This step will typically be performed before the step of forming the first installation unit.

VI. Third Example Reconditioning System

Figure 21:
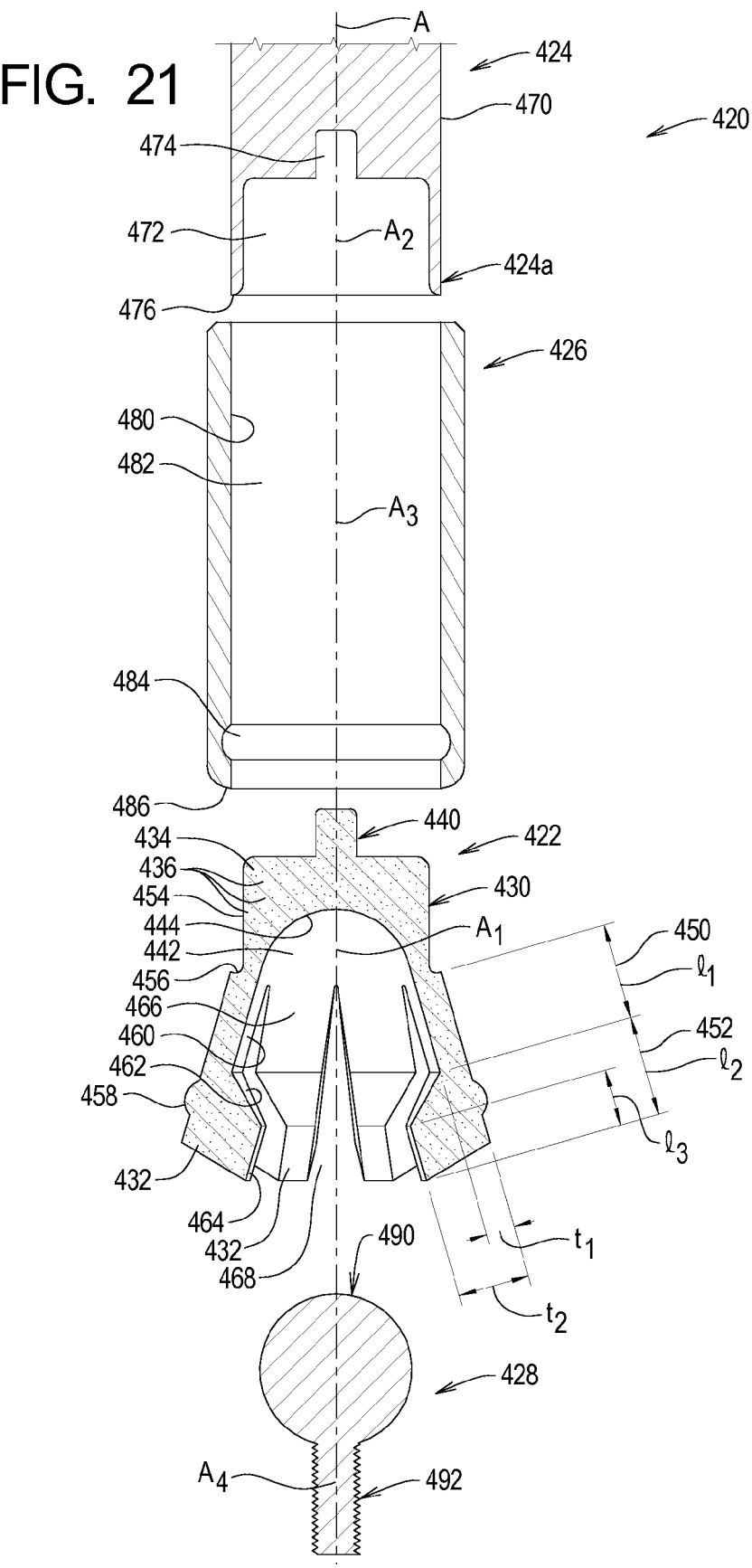
FIG. 21 is an exploded view of a third example reconditioning system of the present invention.

Referring now to FIG. 21 of the drawing, depicted therein is a third example implant reconditioning system 420 constructed in accordance with, and embodying, the principles of the present invention. The example system 420 comprises a buffer member 422, a drive member 424, a sleeve member 426, and a guide member 428. The example implant reconditioning system 420 defines a system axis A.

In use, the guide member 428 supports the buffer member 422 in a desired position relative to an implant to be reconditioned (not shown in FIG. 21). The driver member 424 engages the buffer member 422 and rotates the buffer member 422 relative to the implant. The sleeve member 426 is disengaged to allow the buffer member 422 to be placed in an open configuration in which the buffer member 422 may be arranged in the desired position; the sleeve member 426 is then placed in an engaged position to hold the buffer member 422 is a closed configuration around the implant. As the buffer member 422 is held in the closed configuration around the implant and rotated relative thereto, the buffer member 422 causes the implant member to be reconditioned.

The example buffer member 422 comprises a base portion 430 and a plurality (two or more) of fingers 432 and defines a buffer member axis $A_1$.

The example buffer member 422 comprises a base material 434 coated and/or at least partly embedded with an abrasive material 436. The base material 434 may be any material that is capable of being machined or molded to form the buffer member 422 as described herein and holding that basic shape while axially rotated at speeds sufficient to abrade the implant as discussed herein. The base material 434 should also be sufficiently resilient to allow the example buffer member 422 to be deformed as described below.

While the base material 434 itself may have some abrasive or scrubbing properties, the abrasive material 436 will typically be more abrasive and will remove more of the undesired portion of the implant. The base material 434 of the example buffer member 422 is embedded with the abrasive material 436 so that, if and when the base material 434 wears away, more abrasive material 436 is exposed to abrade the implant. Example abrasive materials include industrial diamond particles and/or silicon carbide, but any material capable of abrading an implant as described herein may be used in addition or instead as the abrasive material 436. And as described above, a slurry containing abrasive material may be used in conjunction with the buffer member 422 to enhance the abrasion of the implant.

A drive boss 440 extends from the base portion 430 generally along the buffer member axis $A_1$. The drive boss 440 is longer in a first lateral direction than in a second lateral dimension; the exact shape of the drive boss 440 is, however, not critical so long as it functions to transfer torque as described below.

An interior surface 442 of the base portion 430 defines a seat surface 444. The seat surface 444 is generally circular and symmetrically arranged about the buffer member axis $A_1$.

The fingers 432 comprise extension portions 450 and tip portions 452. Formed on an outer surface 454 of the buffer member 422 are a step surface 456 (at the base of the fingers 432) and sleeve detent(s) 458 (on the tip portions 452 of the fingers 432).

The extension portions 450 define first inner surface portions 460, while the tip portions 452 define second and third inner surface portions 462 and 464. The second surface portions 462 extend between the first and third inner surface portions 460 and 464 of each of the fingers 432.

The extension portions 450 have a first thickness dimension t1 and a first length dimension l1 and the tip portions 452 have a second thickness dimension t2 and a second and third length dimensions l2 and l3. For reasons that will become apparent from the following discussion, the relative dimensions of the extension portions 450 and tip portions 452 are typically selected based on the dimensions of the implant to be reconditioned.

The buffer member 422 is configured such that the fingers 432 can be moved between an open configuration and a closed configuration. Typically, the entire buffer member 422 is made of a resilient material that can be deformed to move the fingers 432 between the open and closed configurations.

With the example buffer member 422 in the closed configuration, the first, second, and third inner surface portions 460, 462, and 464 are arranged to define substantially contiguous first, second, and third buffer surfaces, respectively, and these buffer surfaces define a buffer chamber 466. In addition, the third buffer surface 464 defines a buffer opening 468.

In the closed configuration, the first inner surface portions 460 of opposing fingers 432 are spaced from each other a distance greater than a distance between the third inner portions 464 of the opposing fingers 432. Also, in the closed configuration the example first and third inner surface portions 460 and 464 are substantially parallel to the buffer system axis $A_1$, while the second inner surface portions 462 are angled with respect to the buffer axis $A_1$.

The example drive member 424 comprises an elongate shaft 470 defining a drive axis $A_2$. The drive member 424 further defines a base cavity 472, a boss cavity 474, and a proximal edge 476. The base cavity 472 is substantially symmetrically arranged along the drive axis $A_2$. Like the drive boss 440, the boss cavity 474 is longer in a first lateral direction than in a second lateral dimension. Further like the drive boss 440, the exact shape of the boss cavity 474 is not critical. Although the exact shapes of the drive boss 440 and boss cavity 474 are not important, the boss cavity 474 should receive the drive boss 440 such that axial rotation of the drive member 424 is efficiently transferred to the buffer member 422 as will be described in further detail below.

The example sleeve member 426 defines a drive axis $A_3$ and an interior wall 480; the interior wall 480 in turn defines a sleeve passageway 482. Formed in the interior wall 480 towards one end of the sleeve passageway 482 is a detent groove 484. The sleeve member 426 defines a proximal end edge 486.

The example guide member 428 defines a guide axis $A_4$ and comprises a seat portion 490 and an anchor portion 492. The seat portion 490 is sized and dimensioned to engage the seat surface 444 of the buffer member 422. The example anchor portion 492 is threaded to engage the implant to be reconditioned as will be generally described elsewhere in this application.

The example implant reconditioning system 420 is assembled generally as follows. The anchor portion 492 of the guide member 428 is engaged with the implant (not shown), and the buffer member 422 is attached to the drive member 424 to form a first installation unit. The first installation unit is then attached to the sleeve member 426 to form a second installation unit. The second installation unit is then placed over a portion of the guide member 428 supported by the implant.

To attach the buffer member 422 to the drive member 424, the buffer member 422 and drive member 424 are then arranged such that the buffer axis $A_1$ and drive axis $A_2$ are aligned with each other. The buffer member 422 is then displaced relative to the drive member 424 such that the base portion 430 of the buffer member 422 is inserted into the base cavity 472 of the drive member 424. When the base portion 430 is fully received within the base cavity 472, the drive boss 440 is also received within the boss cavity 474. Additionally, the proximal end edge 476 of the drive member 424 engages the step surface 456 when the base portion 430 is completely received within the base cavity 472. At this point, the first installation unit is formed.

After the buffer member 422 has been attached to the drive member 424, the sleeve member 426 is arranged such that the sleeve axis $A_3$ is aligned with the buffer axis $A_1$ and the drive axis $A_2$. The buffer member 422 and drive member 424 are then displaced such that the distal end 424a of the drive member 424 enters the sleeve passageway 482.

The second installation unit is initially in a pre-installation configuration in which the buffer member 422 is in the open configuration. By displacing the sleeve member 426 relative to the buffer member 422 such that the sleeve detent(s) 458 enter the detent groove 484, the second installation unit may be placed into an installation configuration.

The buffer member 422, drive member 424, and sleeve member 426 forming the second installation unit in the pre-installation configuration are then displaced such that the seat portion 490 is within the buffer chamber 466. Because the second installation unit is in the pre-installation configuration (i.e., the buffer member 422 is in the open configuration), the seat portion 490 may pass between the fingers 432 of the buffer member 422. After the seat portion 490 is arranged within the buffer chamber 466, the sleeve member 426 is displaced to place the second installation unit in the installation configuration (i.e., the buffer member 422 is in the closed configuration). At this point, the seat portion 490 is arranged within the buffer chamber 466 such that the surface 444 may contact the seat portion 490.

With the second installation unit in the installation configuration and the seat portion 490 of the guide member 428 within the buffer chamber 466 of the buffer member 422, the example reconditioning system 420 is in a use configuration. In the use configuration, axial rotation of the drive member 424 causes axial rotation of the buffer member 422. In general, axial rotation of the buffer member 422 causes the implant being reconditioned to be abraded.

For example, the tip portions 452 of the fingers 432 may abrade the implant directly and/or the tip portions 452 may cause an abrasive material to abrade the implant indirectly.

The third example reconditioning system 420 is or may be used in the same basic manner as the first and second reconditioning systems 20 and 220 described above.

VII. Additional Considerations

Described above are first and second embodiments of implant reconditioning systems and first and second embodiments of methods of reconditioning implants using the first and second implant recondition systems, respectively. It should be apparent that certain features of the first embodiment may be used in the second embodiment and that certain features of the second embodiment may be used in the first embodiment. Examples of variations on the embodiments described above may include the following.

The first system embodiment employs a buffer chamber shaped generally to conform to the shape of the implant being reconditioned. The buffer chamber of the second system embodiment may be similarly shaped.

An irrigation passageway similar to that formed by the first system embodiment may be incorporated into the second system embodiment, and the first system embodiment may be configured to operate without an irrigation passageway.

The first system embodiment may be provided with bristles such as those of the second system embodiment.

More bristles may be provided, and these bristles may be angled as appropriate to facilitate abrading of a given implant member.

And both the first and second method embodiments may be varied to allow the buffer member to be displaced within a short, predefined range of movement to facilitate abrading of the entire desired portion of the implant outer surface.

The scope of the present invention should thus be determined by the claims appended hereto and not the foregoing detailed description of the example embodiments of the invention.

What is claimed is:

1. A system for reconditioning, in situ, a dental implant defining an implant axis and comprising a first implant portion, a second implant portion, and an implant outer surface, where the first implant portion is located farther from the implant axis than the second implant portion, and where a texture layer is formed on at least a textured portion of the implant outer surface, comprising:
    a buffer member defining a buffer axis and a plurality of fingers, where the buffer member is operable in
        an open configuration in which the buffer member may be placed over a portion of the implant, and
        a closed configuration in which the buffer member is in contact with the portion of the implant
    a drive member adapted to engage the buffer member such that rotation of the drive member is transferred to the buffer member;
    abrasive material capable of abrading the implant to remove at least a portion of the implant; and
    a sleeve member, where the sleeve member moves between first and second positions relative to the buffer member; whereby
    the buffer member is in the open configuration when the sleeve member is in the first position;
    the sleeve member holds the buffer member in the closed configuration when the sleeve member is in the second position; and
    rotation of the drive member with the drive member engaged with the buffer member and the buffer member in the closed configuration causes rotation of the buffer member such that the plurality of fingers of the buffer member cause the abrasive material to remove at least a portion of the texture layer on the textured portion of implant outer surface of the second implant portion.

2. A system as recited in claim 1, in which:
    a detent is formed on one of the buffer member and the sleeve member; and
    a groove is formed on the other of the buffer member and the sleeve member;
        wherein the groove receives the detent to releasably secure the sleeve member in the second position.

3. A system as recited in claim 1, further comprising a guide member, where the guide member is detachably attached to the implant to limit movement of the buffer member relative to the implant.

4. A system as recited in claim 3, in which:
    the guide member defines a guide portion; and
    the buffer member defines a seat surface; whereby
    the guide portion engages the seat surface to limit a depth of movement of the buffer member relative to the implant.

5. A system as recited in claim 4, in which the guide portion and seat surface are contoured to allow movement of a buffer member axis defined by the buffer member relative to an implant axis defined by the implant.

6. A system as recited in claim 3, in which:
    a drive passageway is formed in the drive member;
    a buffer passageway is formed in the buffer member;
    at least one guide passageway is formed in the guide member; and
    the drive passageway, the buffer passageway, the at least one guide passageway are aligned to define an irrigation passageway through which material may be introduced between the buffer member and the implant.

7. A system as recited in claim 1, in which the buffer member is deformable such that the fingers move relative to the buffer axis to define the open configuration and the closed configuration.

8. A system as recited in claim 1, in which:
    a drive passageway is formed in the drive member;
    a buffer passageway is formed in the buffer member; and
    the drive passageway and the buffer passageway are aligned to define an irrigation passageway through which material may be introduced between the buffer member and the implant.

9. A system as recited in claim 1, in which:
    a drive boss is formed on the buffer member; and
    a boss cavity is formed in the drive member; wherein
    the boss cavity receives the drive boss such that axial rotation of the drive member causes axial rotation of the buffer member.

10. A system as recited in claim 1, in which the abrasive material is arranged in a slurry that is arranged between the buffer member and the implant.

11. A system as recited in claim 1, in which the abrasive material is embedded within the buffer member.

12. A system as recited in claim 1, in which the buffer member is coated with the abrasive material.

13. A system for reconditioning, in situ, a dental implant defining an implant axis and comprising a first implant portion, a second implant portion, and an implant outer surface, where the first implant portion is located farther from the implant axis than the second implant portion, and where a texture layer is formed on at least a textured portion of the implant outer surface, comprising:
- a buffer member defining a buffer axis and a plurality of fingers, where the buffer member is operable in
  - an open configuration in which the buffer member may be placed over a portion of the implant, and
  - a closed configuration in which the buffer member is in contact with the portion of the implant
- a drive member adapted to engage the buffer member such that rotation of the drive member is transferred to the buffer member;
- abrasive material capable of abrading the implant to remove at least a portion of the implant; whereby
- a drive passageway is formed in the drive member;
- a buffer passageway is formed in the buffer member; and
- the drive passageway and the buffer passageway are aligned to define an irrigation passageway through which material may be introduced between the buffer member and the implant; and
- rotation of the drive member with the drive member engaged with the buffer member and the buffer member in the closed configuration causes rotation of the buffer member such that the plurality of fingers of the buffer member cause the abrasive material to remove at least a portion of the texture layer on the textured portion of implant outer surface of the second implant portion.

14. A system as recited in claim 13, in which:
a drive boss is formed on the buffer member; and
a boss cavity is formed in the drive member; wherein
the boss cavity receives the drive boss such that axial rotation of the drive member causes axial rotation of the buffer member.

15. A system as recited in claim 13, in which:
a detent is formed on one of the buffer member and the sleeve member; and
a groove is formed on the other of the buffer member and the sleeve member;
wherein the groove receives the detent to releasably secure the sleeve member in the second position.

16. A system as recited in claim 13, further comprising a guide member, where the guide member is detachably attached to the implant to limit movement of the buffer member relative to the implant.

17. A system as recited in claim 16, in which:
the guide member defines a guide portion; and
the buffer member defines a seat surface; whereby
the guide portion engages the seat surface to limit a depth of movement of the buffer member relative to the implant.

* * * * *